(12) United States Patent
Fusetti et al.

(10) Patent No.: US 7,979,216 B2
(45) Date of Patent: Jul. 12, 2011

(54) METHOD FOR DETERMINING A GAS COMPOSITIONAL ORIGIN FROM CARBON MATERIAL THERMAL DEGRADATION

(75) Inventors: Luc Fusetti, Condat-sur-Vienne (FR); Françoise Behar, Paris (FR); François Lorant, Thiais (FR)

(73) Assignee: IFP, Cedex (FR)

( * ) Notice: Subject to any disclaimer, the term of this patent is extended or adjusted under 35 U.S.C. 154(b) by 328 days.

(21) Appl. No.: 12/113,243

(22) Filed: May 1, 2008

(65) Prior Publication Data
US 2008/0306695 A1 Dec. 11, 2008

(30) Foreign Application Priority Data
May 4, 2007 (FR) .................................... 07 03262

(51) Int. Cl.
*G01N 25/22* (2006.01)
*G01N 33/24* (2006.01)
(52) U.S. Cl. ............... 702/27; 702/30; 702/11; 702/179
(58) Field of Classification Search .................... 702/11, 702/13, 22–24, 27, 30–32, 136; 703/6, 10–12; 436/59, 56, 145, 155, 804
See application file for complete search history.

(56) References Cited

U.S. PATENT DOCUMENTS
7,153,688 B2 * 12/2006 Mango ............................ 436/32

OTHER PUBLICATIONS
French Search report, FR 0703262, Jan. 4, 2008.

F. Mango, et al., "The carbon isotopic composition of catalytic gas: A comparative analysis with natural gas", Geochimica et Cosmochimica Acta, vol. 63, No. 7/8, pp. 1097-1106, Jan. 1999.
F. Behar, et al., "Thermal Evolution of Crude Oils in Sedimentary Basins: Experimental Simulation in a Confined System and Kinetic Modeling", Revue de L'Institut Francais du Petrole, vol. 46, No. 2, Mar.-Apr. 1991.
F. Behar, et al., "Thermal Stability of Source Rock and Oil Asphaltenes: Comparison With Kerogen Kinetics in Open System Pyrolysis", IV ALAGO Workshop—Basin Modeling, Oct. 16-19, 2005.
F. Lorant, et al., "Carbon isotopic and molecular constraints on the formation and the expulsion of thermogenic hydrocarbon gases", Chemical Geology 147 (Jan. 1998)pp. 249-264.
A. Prinzhofer, et al. "Gas Isotopes Tracing: An Important Tool for Hydrocarbons Exploration", Oil & Gas Science and Technology—Rev. IFP, vol. 58 (2003), No. 2, pp. 299-311.

* cited by examiner

*Primary Examiner* — Michael P Nghiem
*Assistant Examiner* — Ricky Ngon
(74) *Attorney, Agent, or Firm* — Antonelli, Terry, Stout & Kraus, LLP.

(57) ABSTRACT

At least one type of carbon material susceptible to generate a gas G is selected. Then, a model is built from the carbon isotopic composition of a gas P generated by thermal degradation of this type of carbon material. The model is calibrated by calibrating the kinetic effect independently of the precursor effect. In order to achieve that, pyrolyses are performed on compounds modeling the type of carbon material, said compounds being synthesized and labeled with $^{13}C$. Using said model, a carbon isotopic composition of gas P generated is estimated. Finally, it is determined whether gas G has been generated from the selected type of carbon material, by comparing a measured isotopic composition of gas G to the estimated isotopic composition.

4 Claims, 4 Drawing Sheets

METHOD FOR DETERMINING A GAS COMPOSITIONAL ORIGIN FROM CARBON MATERIAL THERMAL DEGRADATION

This invention concerns the oil exploration and production sector. In particular the invention has for object a method to determine, by thermal degradation, the type of carbon compounds (oil, kerogen) at the origin of the genesis of a gas extracted from the subsoil.

The method relies on a carbon isotopic fractionation model for reactions such as oil thermal cracking.

In nature, sedimentary material degradation into gas results from two phenomena, thermal maturation and biodegradation. The biodegradation takes place at shallow depths, at temperatures at which bacteria are not destroyed. For deeper burial of organic material, kerogen can undergo a first degradation, called "early primary", that produces the genesis of an early gas associated at the same time with that of oil. Then, by the end of the oil window, kerogen, as well as hydrocarbons generated during the previous phase and retained in the rock, are undergoing a new thermal cracking producing a gas called "late primary". Finally, it is possible that oil, expelled from the mother rock during the early primary cracking, has continued to sink down. It could then meet temperatures sufficiently high to bring its degradation into smaller structures, including a so-called secondary gas. Hence, gases produced by operators can have five origins.

Migration phenomena can result in a mixture of different gas types previously generated within the reservoir rock, influencing the gas quantity and quality in the location. The stake linked to determining the gas various origins is therefore critical for oil companies in term of prospection, with regards to the very significant costs generated by exploration policies, particularly at sediment depths seen with high pressure-high temperature reservoirs. From gas origin can depend the site of the future drillings, their depths, . . .

STATE OF THE TECHNIQUE

To achieve it, known methods are based on an isotopic tool for modeling the isotopic fractionation of oil thermal cracking. Indeed, carbon isotopic fractionation, generated by the gas production, is not the same according to its genesis route. Gas genesis from an oil results in an important isotopic $^{13}C$ gas enrichment. Other generated or residual fractions ($C_6C_{14}$, $C_{15}$-$C_{20}$, C20+, residues) have $^{13}C$ isotopic composition variations one order of magnitude lower and not necessarily unidireactional (not just enrichment or not just impoverishment in $^{13}C$)

An element's isotopes have appreciably different physical and chemical properties. The discrimination between isotopes along chemical, biochemical reactions and physical processes constitutes the isotopic fractionation. The isotopic fractionation concept accounts for an element's isotopic composition variations.

The influence of degradation by thermal maturation on the isotopic composition of the gases generated can be expressed as resulting from two effects the first one, called precursor effect (or source term), is linked to the distribution of an element's isotopes within a given molecule. Indeed, carbon for instance has two stable isotopes, carbon 12 and carbon 13 of which respective mean percentages within natural organic molecules are in the order of 98.9% and 1.1%. However, these are mean percentages and, even within one same natural molecule, this distribution may vary significantly. It has been shown in particular that for substituted aromatic hydrocarbons, carbon 13 concentrates preferentially on the aromatic cycles rather than on the hydrocarbon side chains. Anyway, the composition of a gas at the end of the reaction associated to its genesis should tend toward the initial isotopic composition of its precursors within the structure of the molecule(s) which underwent the degradation. Because of the above mentioned known precursor effect, said isotopic composition of gas precursors is different from that of the molecule containing it.

the second effect responsible for isotopic fractionation, called kinetic effect, reflects the rate difference at breakage time of a given bond between two atoms, when these are a particular isotope of the element under consideration, in this case carbon, rather than another.

The isotopic fractionation phenomenon can be modeled according to two approaches. The first approach reasons in terms of thermodynamic balance of exchange reactions between isotopes of a same element. We can cite i.e., James, A. T., 1983. Correlation of natural gas by use of carbon isotopic distribution between hydrocarbon components. American Association of Petroleum Geologists Bulletin 67(7), 1176-1191.

However, this thermodynamic approach is incapable to account for low $\delta^{13}C$ variations between gases, except at very high temperatures. Thus, it has been shown that the difference calculated between propane and butane $\delta^{13}C$ is 1‰ of what James' model predicts for temperatures under geological conditions above 400° C., which is not realistic.

The second approach studies the kinetic aspect of such phenomenon which results in a difference of instantaneous degradation speeds of $^{12}C$—$^{12}C$ and $^{13}C$—$^{12}C$ bonds.

Indeed, the isotopic fractionation phenomenon, that occurs during chemical reactions, originates from the reactivity difference in term of kinetics of the different isotopes of a same element. Such difference in reaction constants reflects a difference, in particular at the level of the activation energies associated with these reactions. The known different kinetic models of isotopic fractionation can be classified according to mathematical formalism used to calculate $\delta^{13}C$ and reactional schemes taken in account.

The Distillation Models

These approaches often describe isotopic fractionations globally by a single reaction without actual kinetic consideration. The isotopic compositions of the gas and its source as a function of the degree of advancement of the reaction follow explicitly Rayleigh's law. An example of such a model is given by Berner, U., Faber, E., Scheeder, G., Panten, D., 1995. Primary cracking of algal and land plant kerogens: kinetic modeling of kerogen and oil cracking. Organic Geochemistry 126, 233-245.

However, the models based on Rayleigh's law cannot be extrapolate to geological conditions, since this formalism supposes isotopic fractionation coefficient to be temperature independent. Indeed, the isotopic fractionations observed in laboratory are much lower than those observed for much longer times and at lower temperatures under geological conditions.

The Kinetic Models

This second type of approach is indeed an actual kinetic approach in the sense that it is exclusively based on first order kinetics. In relation to the previous approach this one has the advantages of expliciting the reactional mechanisms applied for oil and gas formation and, the $^{12}C$ and $^{13}C$ balance being calculated from discreet equations, $\delta^{13}C$ can be simulated for both $C_2$-$C_4$ formation and secondary cracking. An example of such a model is given by Cramer, B., Faber, E., Gerling, P., Krooss, B. M., 2001. Reaction Kinetics of Stable Carbon Isotopes in Natural Gas-Insights from Dry, Open System Pyrolysis Experiments. Energy and Fuels 15, 517-532.

Tang, Y., Huang, Y., Ellis, G. S., Wang, Y., Kralert, P., Gillaizeau, B., Ma, Q., Hwang, R., 2005. A kinetic model for thermally induced hydrogen and carbon isotope fractionation of individual n-alkanes in crude oil. Geochimica et Cosmochimica Acta 69 (18), 4505-4520.

The Statistical Models

The last type of approach is based on statistical calculations. Waples and Tornheims finalized a model of hydrocarbon gas genesis during n-alkane cracking, where the reagent and product isotopic compositions result from a statistical treatment of $^{12}C$—$^{12}C$, $^{12}C$—$^{13}C$, and $^{13}C$—$^{13}C$ bond breakages as a function of time.

Waples, D. W., Tornheim, L., 1978. Mathematical models for petroleum-forming processes: n-paraffins and isoprenoid hydrocarbons. Geochimica Cosmochimica Acta 42, 457-465.

Waples, D. W., Tornheim, L., 1978. Mathematical models for petroleum-forming processes: carbon isotope fractionation. Geochimica Cosmochimica Acta 42, 467-472.

However, none of the known models helps determine the origin of the gases formed since none of these models can discriminate between precursor and kinetic effects of the isotopic fractionation.

One object of this invention concerns a method to determine the type of carbon compounds (oil, kerogen) at the origin of the genesis, through thermal degradation, of a gas extracted from subsoil. To achieve that, the method is based on an isotopic tool provided for modeling the isotopic fractionation taking place during a carbon mixture cracking, while discriminating precursor and kinetic effects.

THE METHOD ACCORDING TO THE INVENTION

The invention concerns a method to determine the compositional origin of a gas G formed from thermal degradation of carbon materials, wherein at least one type of carbon material susceptible to generate said gas G is selected, and one builds a model of carbon isotopic composition of a gas P generated by thermal degradation of aforesaid type of selected carbon material. The method includes the following steps:

said model of isotopic composition is calibrated by calibrating a reaction kinetic effect independently of a precursor, defined as the carbon isotopic composition effect of said material type on the carbon isotopic composition of said gas P generated, by performing pyrolysis on model compounds of the material type, said compounds being synthesized and $^{13}C$ labeled;

a carbon isotopic composition of gas P generated is estimated, using aforesaid model;

a carbon isotopic composition of aforesaid gas G is measured; and

Finally, it is determined if gas G has been generated from the selected type of carbon material, by comparing said measured isotopic composition to said estimated isotopic composition.

The carbon isotopic composition model can be established by realizing the following steps:

model compounds of aforesaid type of selected carbon material are chosen;

the kinetic effect is calibrated using pyrolyses of synthesized and $^{13}C$ labeled model compounds in order to determine precursor effect;

the precursor effect is calibrated by pyrolyzing a mixture of natural model compounds, once the kinetic effect is calibrated;

the model is extended to the complete composition of said type of carbon material selected, assuming that one of either effects, kinetic or precursor, is the same for any other compound of said mixture; and aforesaid model is extrapolated to geological conditions.

According to the method, the quality of a gas extracted from a subsoil formation can be assessed: by selecting an oil and a kerogen as types of carbon material, and by determining a carbon isotopic composition model of a gas product of the oil, and a carbon isotopic composition model of a gas product of kerogen. Then, using such models, the quality of the gas extracted from the subsoil formation is determined, by assessing proportions, within the gas extracted, of various gases resulting from oil and kerogen.

Other characteristics and advantages of the method according to the invention, will appear hereafter upon reading the description of non restrictive examples of embodiments, and referring to the figures hereafter annexed and described.

BRIEF OVERVIEW OF THE FIGURES

DETAILED DESCRIPTION OF THE METHOD

Figure 1:
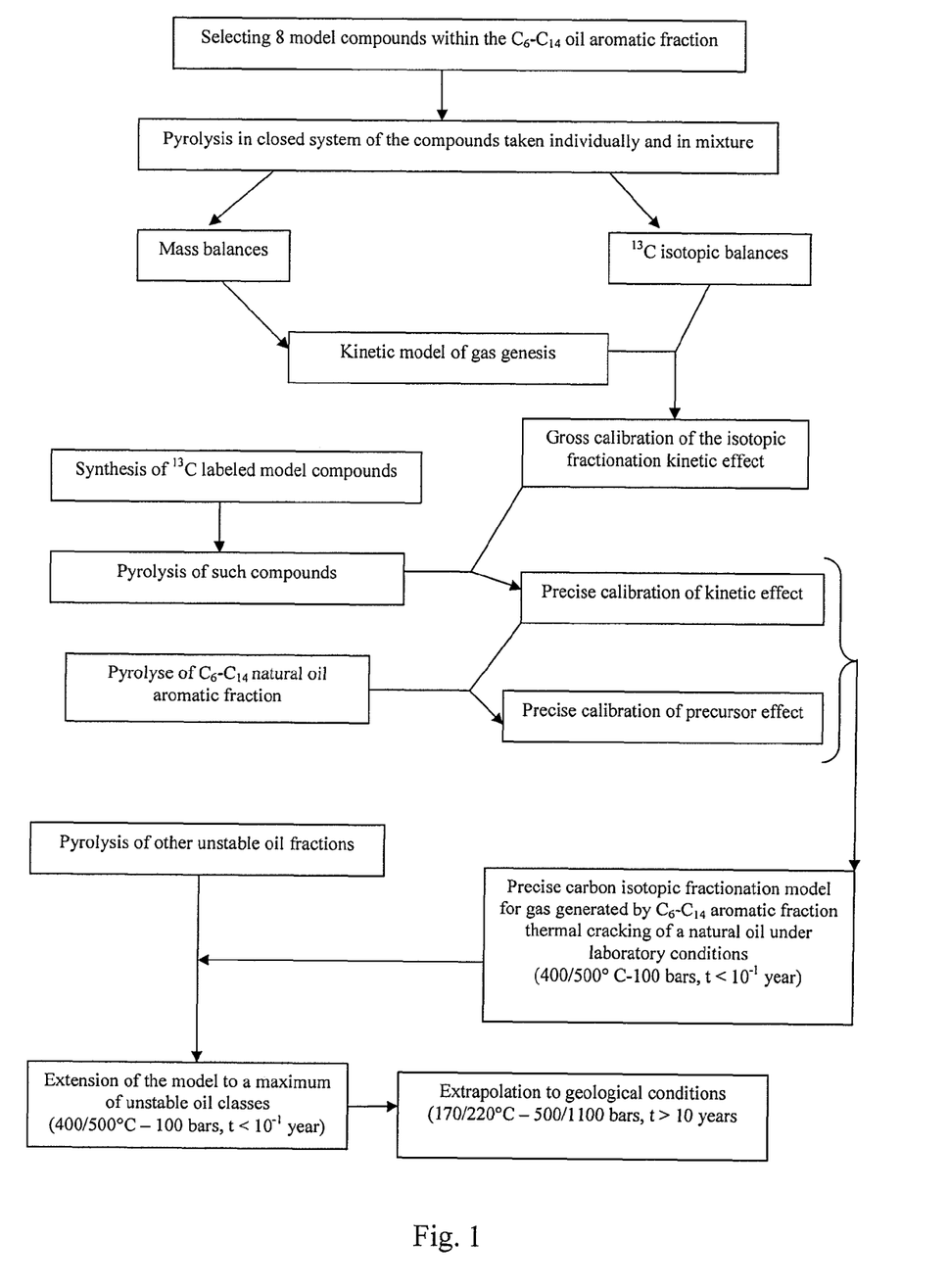
FIG. 1 is a diagram illustrating the calibration steps of the isotopic fractionation model of the invention.

The method according to the invention enables assessment of the quantity and quality of a gas present in a subsoil formation when such gas results from bond breakage between carbon atoms, following a thermal degradation of, i.e., carbon compounds. FIG. 1 is a diagram illustrating the steps of the method.

The method includes defining a model of carbon isotope distribution variation during degradation. Then, said model is calibrated by treating independently the precursor effect and the effect kinetic of isotopic fractionation during thermal degradation. This model is then used to compare isotopic fractionation measurements made on a gas, in order to assess the quantity and quality of said gas extracted from a subsoil formation.

The independent calibration of the isotopic fractionation precursor effect and kinetic effect relies on compound synthesis combined with isotopic labeling. Given a reagent H producing a gaseous product P, the calibration method includes the following steps:

a) choosing model compounds of the reagent;
b) calibrating the kinetic effect through pyrolyzing synthesized and $^{13}$C labeled model compounds in order to determine the precursor effect;
c) calibrating the precursor effect by pyrolyzing a mixture of natural model compounds, once the kinetic effect is calibrated;

1—Building Carbon Isotopic Fractionation Model

Principle

The aim is to establish a carbon isotopic fractionation model when such fractionation is caused by the production of a gas P resulting from a reagent H thermal degradation. An isotopic fractionation model enables to estimating the variation of the carbon isotope distribution during the reagent thermal degradation. It is therefore desirable to establish an isotopic composition model of product P over time.

Product P isotopic composition is noted $\delta^{13}C_P$, and calculated as follows:

$$\delta^{13}C_P = (R_{Cp}/R_{Cstd} - 1)*1000$$

with: $R_{Cp}$: $^{13}C/^{12}C$ mass isotopic ratio of product P
$R_{Cstd}$: $^{13}C/^{12}C$ mass isotopic ratio of standard PDB Definition A fractionation is considered according to the following schematic: product P is generated from the breakage of a $^{12}C$—$^{12}C$ or $^{12}C$—$^{13}C$ bond The reaction is written $R \to p \cdot {}^{13}P+$ $R \to p \cdot {}^{12}P+.$ with: $^{13}P$, product P resulting from $^{12}C$—$^{13}C$ bond breakage
$^{12}P$, product P resulting from $^{12}C$—$^{12}C$ bond breakage It is then considered that $^{13}P$ and $^{12}P$ production reactions follow the same first order rate law as product P production reaction.

A chemical reaction rate reflects reagents H or products P concentration variation over time t. For a reaction of the type $H \Rightarrow p.P+ \ldots$, reagent H disappearance or product P apparition rate is expressed by $$V = -d[H]/dt = (1/p) \cdot d[P]/dt = k \cdot [H]^n$$

with: k: rate constant only depending on temperature T
n: current order of the reaction.

Numerous studies on different compounds show that the first order is suitable to describe the actual reaction. The quantity $Y_{P/H_0}$ of product P generated as a function of time t (in mg per g of initial $H_0$ load) is therefore $$Y_{P/H_0}(t) = Y_\infty [1 - \exp(-k \cdot t)]$$

with: $Y_\infty$, the value toward which Y tends at the end of the reaction.

By realizing these experiences at different temperatures, we verify that k(T) follows the temperature dependence of Arrhenius' law. So we can write:

$$k(T) = A \cdot \exp(-Ea/R \cdot T)$$

with:
A: frequency or pre-exponential factor (in $s^{-1}$ for a first order reaction)
Ea: energy of activation (in $kcal.mol^{-1}$)
R: perfect gas constant (0.001987 $kcal.mol^{-1}.K^{-1}$)
T: absolute temperature (Kelvin)

Figure 2:
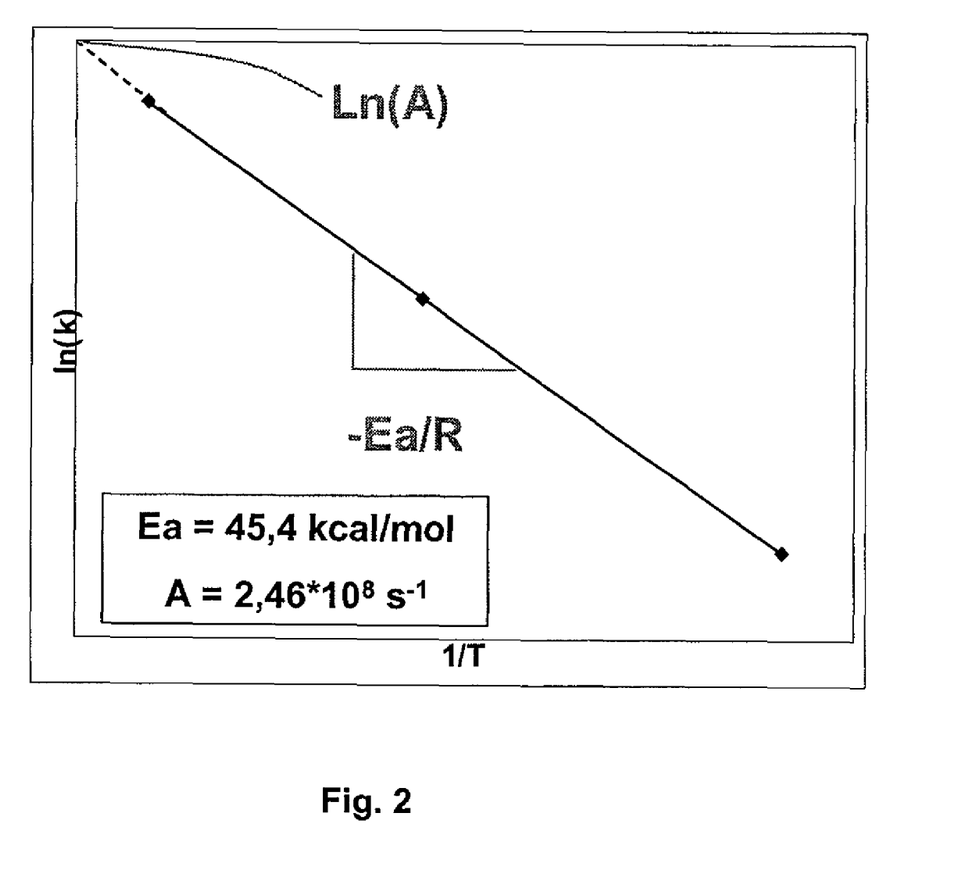
FIG. 2 shows straight line ln(k) as a function of (1/T) with slope (−Ea/R), and ln(A) the ordinate at the origin.

The trace ln(k) as a function of (1/T) is therefore a straight line with slope (−Ea/R) and ordinate at the origin ln(A), as illustrated in FIG. 2. The kinetic parameters (activation energy Ea and frequency factor A) for ethane genesis are therefore determined by repeating pyrolyses at different temperatures, and by determining k.

By applying these laws to the production reactions for $^{13}P$ et $^{12}P$, one obtains:

$$\delta^{13}C_P = [(\delta^{13}C_{P\infty}/1000+1)*(1-\exp(-\alpha \cdot k \cdot t))/(1-\exp(-k \cdot t))-1]*1000$$

with: $\delta^{13}C_{P\infty}$: isotopic composition of product P at the end of the reaction
α: isotopic fractionation coefficient The isotopic fractionation coefficient is expressed by $$\alpha = {}^{13}k/{}^{12}k = {}^{13}A/{}^{12}A \cdot \exp(-\Delta E/R \cdot T)$$

with: $^{12}k$ and $^{13}k$, the rate constants respectively of $^{12}C$—$^{12}C$ and $^{12}C$—$^{13}C$ bond breakage reactions, $^{12}A$ and $^{13}A$, the associate frequency factors, and ΔE, the difference between the associate energies of activation. The ratio $^{13}A/^{12}A$ can be set at 1.02 (classic value).

At the end, the isotopic fractionation model according to the invention is written:

$$\delta^{13}C_P = [(\delta^{13}C_{P\infty}/1000+1)*(1-\exp(-(1.02 \cdot \exp(-(-\Delta E/R \cdot T)) \cdot k \cdot t))/(1-\exp(-k \cdot t))-1]*1000$$

The parameters to be calibrated are therefore
the rate constant: k
the isotopic composition of product P at the end of the reaction: $\delta^{13}C_{P\infty}$
the difference between the associated energies of activation: ΔE.

Calibration

The method according to the invention is described in the context of petroleum development, where oil companies wish to know the hydrocarbon compounds originating the gases they produce through a well. The studied reaction concerns therefore the transformation of oil into gas under the effect of a temperature increase.

a) Choosing the Reagent Model Compounds

Oil is composed of various molecular classes. We shall limit ourselves to a simple unstable molecular class sufficiently representative of the oil chemical composition and of its thermal behavior (herein $C_6$-$C_{14}$ aromatics). Among this molecular class, we choose individual compounds, so called model compounds, which can be purchased very pure commercially and are among those most present in the class under consideration, and which are unstable too (stable compounds are found globally in the so-called unstable class).

Recent publications demonstrate the superior reactivity of aromatic hydrocarbons as compared to their saturated homologues during thermal cracking reactions under geological conditions; it is therefore not necessary to take the latter into consideration for building the model.

On the other hand, a kinetic study on cracking a $C_6$-$C_{14}$ aromatic fraction of a Type-II oil, presented in the following article:

Al Darouich, T., Behar, F., Largeau, 2006. Thermal cracking of the light aromatic fraction of Safaniya crude oil-experimental study and compositional modelling of molecular classes. Organic Geochemistry 37, 1130-1154.

shows that this range of molecular masses characterizes compounds present, others than saturated, which can be identified in detail and quantified by current analytic methods; this corresponds therefore to the original system sought-after for building such model. Indeed, beyond $C_{15}$, the mixture is too complex, and individual quantification of the species present is not possible. Among the molecules identified by this kinetic study, in light aromatic oil cross-section, eight are thus selected for their high degree of representation, as much from the oil composition as from the proportion of gas produced during oil thermal cracking. They belong to methylaromatic and alkylaromatic molecular fractions Such a system of model compounds may represent more than 80% of the thermal cracking of oil's light aromatic fraction. Indeed, some studies have shown that benzene, toluene, xylenes, and sulfured aromatics are stable under study conditions, and therefore do not need to be taken into account for this study. Only naphtene aromatics, contributing 18.5% of a Type-II oil light aromatic fraction, are not taken into account because of they are difficult to synthesize and above all to purify.

b) Calibration of the Kinetic Effect

The kinetic effect is calibrated for each model compound identified. The gas studied is, for example, ethane. The model compound studied is, still as an example, 2-ethyltoluene. The goal is to establish a carbon isotopic fractionation model when such fractionation is due to ethane production from 2-ethyltoluene pyrolysis.

In order to calibrate unknown model parameters (k, $\delta^{13}C_{P\infty}$, $\Delta E$) one pyrolyzes the reagent (2-ethyltoluene molecule) at various temperatures, followed by molecular analyses and isotopic analyses.

Pyrolyses are also performed on an "artificial" mixture of such commercial model compounds in order to quantify a possible mixture effect on kinetics and/or isotopy, which would have to be taken into account in the final model version.

Molecular Analysis: k Determination

Pyrolyses of 2-ethyltoluene molecule (reagent) are realized at various temperatures and for various durations, then the quantity of ethane produced is measured (molecular analyses are realized on different fractions ($C_1$-$C_4$; $C_6$-$C_{14}$; $C_{15}$-$C_{20}$; $C_{20}$+ and on insoluble residual in the DCM). The following 2-ethyltoluene molecule pyrolyses have been realized in this way:

The Xs mean a pyrolysis experiment realized under the corresponding temperature and time.

The kinetic parameters of 2-ethyltoluene into ethane degradation reaction are deducted, by assuming a first order reaction with rate constant k following Arrhenius' law temperature dependence.

Figure 3:
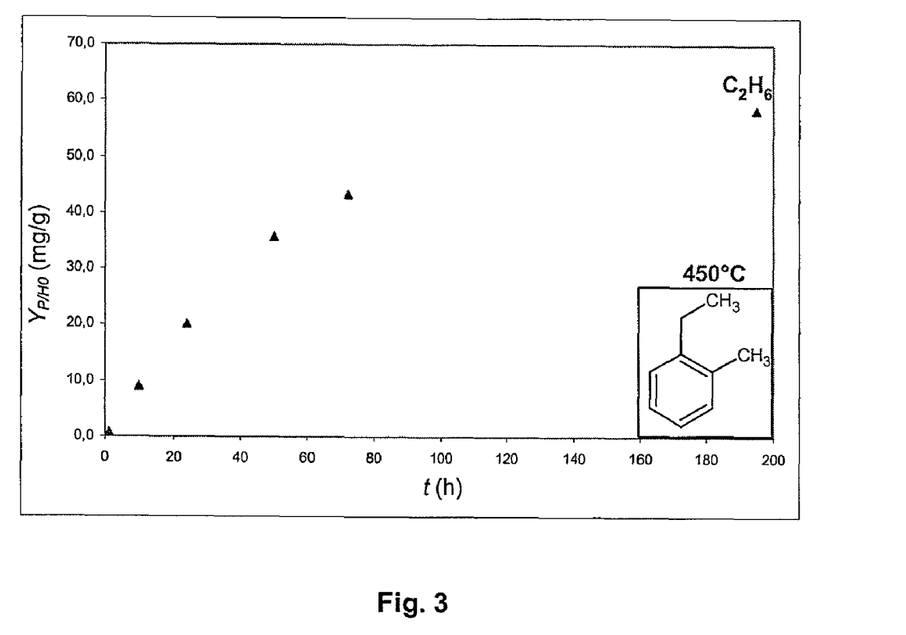
FIG. 3 shows measurements of ethane production as a function of time, at 450° C. temperature.
Figure 4:
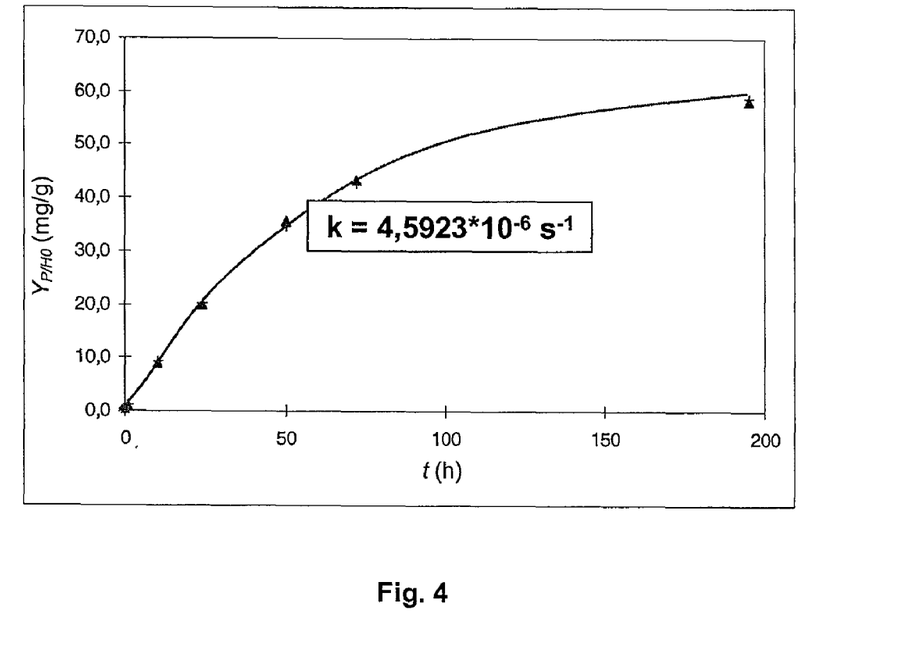
FIG. 4 shows a trace adjustment of the type y=a[1−exp(−x)] to best estimate the observations in FIG. 3, and thus determine k.
Figure 5:
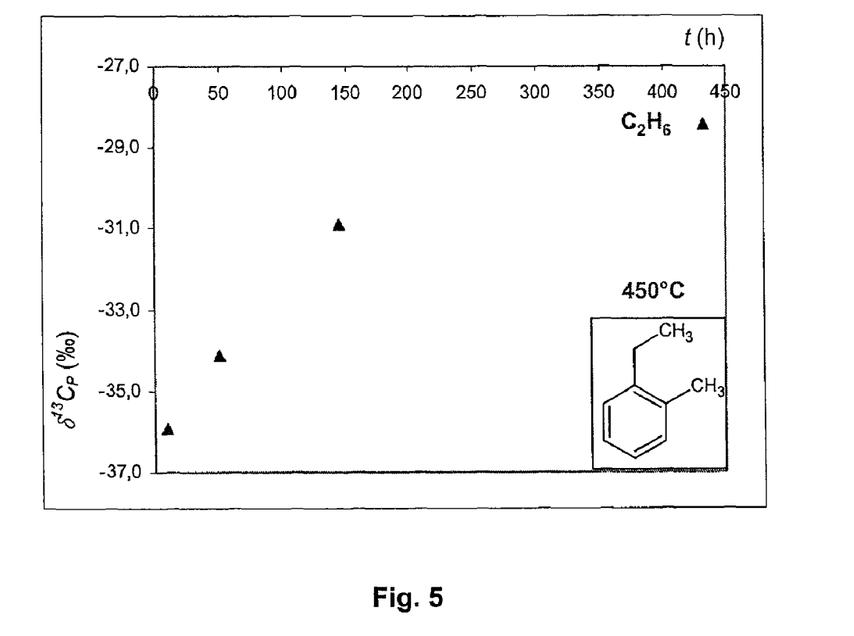
FIG. 5 shows $\delta^{13}C$ measurements as a function of time, at 450° C. temperature.
Figure 6:
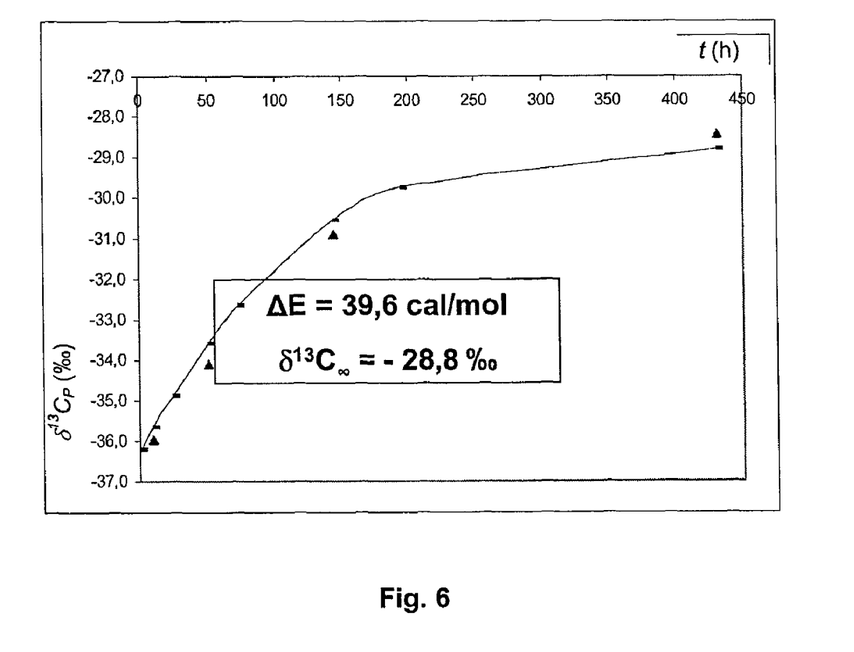
FIG. 6 shows the adjustment of a fractionation model to best estimate the observations in FIG. 5, and thus determine $\Delta E$ and $\delta^{13}C_{P\infty}$.

The rate constant k for ethane genesis is thus calibrated using empirical data. In order to do that, one measures ethane production $Y_{P/H_0}$ as a function of time t, at a given temperature. The production is expressed in mg by g of initial load $H_0$. FIG. 3 shows measurements realized at 450° C. temperature. Then, rate constant k is adjusted so that a curve of the type $y=\alpha[1-\exp(-x)]$ best estimates the observations realized (i.e., by non-linear regression). FIG. 4 illustrates the evaluation in the case of FIG. 3. For 2-ethyltoluene molecule pyrolysis at 450° C., the evaluation provides: $k=4.5923*10^{-6}$ $S^{-1}$ Isotopic Analysis: Determination of $\delta^{13}C_{P\infty}$, and $\Delta E$ 2-ethyltoluene molecule (reagent) pyrolyses are realized at various temperatures. Isotopic analyses are then realized on different fractions ($C_1$-$C_4$; $C_6$-$C_{14}$; $C_{15}$-$C_{20}$; $C_{20}$+ and on insoluble residue in the DCM). Isotopic composition of product P is measured ($\delta^{13}C_P$). FIG. 5 shows $\delta^{13}C_P$ measurements as a function of time, at 450° C. temperature. Then $\delta^{13}C_{P\infty}$ parameters are adjusted so that a trace representing $\delta^{13}C_P$ model best estimates the observations made (i.e., by non-linear regression). FIG. 6 illustrates the evaluation in the case of FIG. 5. The trace represents the equation $$\delta^{13}C_P = [(\delta^{13}C_{P\infty}/1000+1)*(1-\exp(-(1.02-\exp(-\Delta E/R \cdot T)) \cdot k \cdot t))/(1-\exp(-k \cdot t))-1]*1000$$

with: $\delta^{13}C_{P\infty}$: $-28.8$‰ and $\Delta E$: 39.6 cal/mol

However, these $\delta^{13}C_P$ and $\Delta E$ values are obtained simultaneously. $\Delta E$ is therefore obtained without precisely knowing the precursor effect, modeled by $\delta^{13}C_{P\infty}$: $\delta^{13}C_{P\infty}$ evolution curve as a function of time is a correctly estimated form but the kinetic effect calibration should be improved initially.

Therefore, this model is not reliable enough to discriminate a gas origin. In order to improve the quality of the model, the precursor effect should be constrained in order to model $\delta^{13}C_P$ isotopic composition evolution with the greatest precision possible, i.e. the kinetic effect.

Then, the model should be adapted to natural samples. Indeed, the isotopic composition evolution curve is translated for a natural compound with regards to the commercial compound, because their synthetic history (the way they were formed) is different (meaning that their precursor effects are different, although their kinetic effects are identical). According to the invention, the precursor effect is constrained by realizing a synthesis of model compounds during which 100% of the carbon 13 isotope is implanted into precise locations of their carbon skeleton, thus pegging geochemical markers before thermal cracking. Indeed, commercially available molecules do not provide advance isotopic composition knowledge of their various constituting groups because the syntheses routes are kept confidential and intermediates are not provided. On the other hand, a synthesis route as that presented here may solve this problem.

| | t(h) | | | | | | | | | | | | |
|---|---|---|---|---|---|---|---|---|---|---|---|---|---|
| T(° C.) | 1 h | 3 h | 6 h | 10 h | 18 h | 24 h | 50 h | 72 h | 120 h | 144 h | 195 h | 216 h | 432 h | 648 h |
| 395 | | | | | | x | | x | | | x | x | x | |
| 425 | | x | x | | | | x | | | | x | | | x |
| 450 | x | | x | x | x | | x | x | | | x | | | |

The synthesis also mimics "in reverse" the carbon cycle cracking steps that occurred during pyrolysis by associating, to built the molecule, groups that will be the same as those produced during pyrolysis thermal cracking. Such a synthesis enables therefore, provided the precursor of each gas is known, to predict with precision the isotopic composition that the gas will reach at the end of the reaction (the precursor effect).

2-ethyltoluene is thus synthesized. The following reaction can be used:

MgICl

Precursor effect $\delta^{13}C_{P\infty}$ being perfectly constrained through this synthesis route combined to an isotopic labeling, kinetic effect $\Delta E$ is precisely calibrated using pyrolysis isotopic data of said labeled compound ($\Delta E$ being adjusted). These data are obtained as previously described. Pyrolyses of molecules synthesized and labeled as previously mentioned are performed at different temperatures, and isotopic analyses are conducted in order to determine $\Delta E$. Indeed, in the previous $\delta^{13}C_p$ model, $\delta^{13}C_\infty$ is now determined, and α alone (via $\Delta E$) can be adjusted. FIGS. 5 and 6 illustrate an example at 450° C.

The results obtained for each labeled model compound are pooled to obtain an isotopic fractionation kinetic effect model of the $C_6$-$C_{14}$ aromatic fraction: all $\Delta E$ are adjusted for all model compounds providing a $\Delta E$ range that constitutes a global model of the $C_6$-$C_{14}$ aromatic fraction. In fact, a model is built for each compound and the global model groups all these models together.

In order to verify that all data are precise enough to elaborate such a model, the measurements are completed with mass and isotopic balances.

c) Calibration of the Precursor Effect

Then, the precursor effect is precisely determined relative to the natural compounds constituting the $C_6$-$C_{14}$ oil fraction. To achieve this, a $C_6$-$C_{14}$ oil aromatic cross-section is pyrolyzed, and $\delta^{13}C_\infty$ is calibrated by applying the previous model obtained from the $\Delta E$. It is considered that for a fixed molecule, the isotopic fractionation kinetic effect is the same, whether for a natural molecule or a commercial synthetic molecule. Only precursor effects change. A model is thus obtained, calibrated with great precision and describing the isotopic fractionation of the gases generated during the $C_6$-$C_{14}$ aromatic fraction thermal cracking of a natural oil.

Extension of the Model to Natural Samples

The model is then extended to other unstable oil molecular fractions. Frequency factors A and activation energies Ea can be determined using the method described in the following patent applications: FR EN/06/08.717 and FR EN/06/08.715.

One supposes then that either $\Delta E$ or $\delta^{13}C_\infty$ parameters, determined for the $C_6$-$C_{14}$ natural aromatic fraction, is the same for each new unstable fraction considered. If the calibration of the other parameter using isotopic measurements resulting from such a fraction pyrolysis enables to modeling the experimental results correctly, the result is validated. Therefore, one obtains an isotopic fractionation model for the gas generated by oil thermal cracking, but for time/temperature conditions met in laboratory.

Extrapolation of the Model to Geological Conditions

Finally, the model is extrapolated to geological conditions, meaning for lower temperature conditions (between 140° C. and 220° C. in case of an oil secondary cracking) and for longer periods of time (several millions or dozens of millions years). The model thus predicts the isotopic fractionation of ethane generated by oil thermal cracking in the reservoir.

To achieve that, different $\Delta E$ and $\delta^{13}C_\infty$ values being known, one chooses such orders of magnitude for T and t in the α and $\delta^{13}C_p$ formulas.

In a very simplified way, if $\delta^{13}C_p$ variation observed for ethane produces by 422 h of 2-ethyltoluene pyrolysis at 450° C. is +7.5‰, then it becomes +22.2‰ if the same compound is pyrolyzed at 180° C. for 5 millions years.

2—Evaluation of the Quantity and Quality of a Gas Derived from a Reservoir

After validation with gas natural samples of known origin, the model can be applied to study natural cases when prospecting for gas and oil. With such a model, it becomes possible then, by measuring the carbon isotopic composition of the gas in a reservoir, to identify the part derived from oil thermal cracking.

An oil company, after drilling a well through a gas reservoir, performs a carbon isotopic measurement of the gas extracted. The company geologists knowing the thermal history of the basin, the isotopic fractionation model according to the invention is used to determine what would be the composition of a secondary gas from cracking an oil that would have undergone such a thermal maturation. In order to do that, one chooses a type of oil as reagent and model compounds, then calibrates the model, and applies it to estimate the $\delta^{13}C_p$ gas isotopic composition at a time t provided from the basin thermal history, as if such gas came exclusively from the oil selected. By comparing this value to the actual value, one can deduct its secondary gas proportion (from the oil) within the actual gas mixture in the reservoir. From calibrating the model by replacing the oil as reagent by kerogen, a model is established for early primary and late primary gases. Then, the proportion of these gases is determined. Indeed, we have a system of two equations with two unknowns: the global gas isotopic composition $\delta^{13}C_G$ is measured and each gas isotopic compositions ($\delta^{13}C_{G1}$ and $\delta^{13}C_{G2}$) are modeled. Given x the primary gas percentage and y the secondary gas percentage, we have a first equation: x+y=100. In addition $$x*\delta^{13}C_{G1}+Y*\delta^{13}C_{G2}=100*\delta^{13}C_G$$

Therefore, x and y can be determined. The quality of a gas produced in a well is thus directly established, i.e. determining the proportions of the various gases resulting from various sources.

Finally, if geologists know the quantity of the various sources (the original kerogen and/or oil quantity) then only the kinetic model itself can determine the quantity of each gas.

The information contributed by such models coupled to basin modeling are quite important for future prospective orientation toward a more gas or more oil thematic, and for reducing the risk of dry wells. From gas origin, can depend the site of future drillings, their depths, . . .

Applications of the Isotopic Fractionation Model

The isotopic fractionation model according to the invention can be applied to all processes generating differentiated C—C bond breakages as a function of the carbon isotopes present, namely when the generated isotopic fractionation results from both a kinetic effect and a precursor effect.

Thermal cracking processes may be mentioned, such as refining and combustion, as well as oil or kerogen bacteriological degradation processes yielding gas (among others). All such processes indeed generate a carbon isotopic fractionation that results from a kinetic effect and a precursor effect.

The invention claimed is:

1. Method for determining the compositional origin of a gas G from thermal degradation of carbon materials, wherein at least one carbon material type susceptible to generate the gas G is selected, and a model of carbon isotopic composition is built for a gas P generated by thermal degradation of the selected carbon material type, characterized in that the following steps are performed:
   the model of carbon isotopic composition is calibrated by calibrating a kinetic effect of reaction independently of a precursor effect, defined as a carbon isotopic composition effect of the carbon material type on a carbon isotopic composition of the gas P generated, by:
      synthesizing model compounds of the carbon material type, each of the model compounds being an individual compound of an unstable molecular class representative of a chemical composition of the carbon material type and representative of a thermal behavior of the carbon material type;
      $^{13}C$ labeling the model compounds that have been synthesized; and
      pyrolyzing the model compounds that have been synthesized and labeled;
   a carbon isotopic composition of gas P generated is estimated, using the model of carbon isotopic composition;
   a carbon isotopic composition of the gas G is measured; and
   it is determined whether gas G has been generated from the selected carbon material type, by comparing the measured isotopic composition to the estimated isotopic composition.

2. Method according to claim 1, wherein one selects an oil and a kerogen as carbon material types, and one determines a model of carbon isotopic composition of a gas derived from oil, and a model of carbon isotopic composition of a gas derived from kerogen, and one determines, using the model of carbon isotopic composition of a gas derived from oil and the model of carbon isotopic composition of a gas derived from kerogen, a quality of a gas extracted from a subsoil formation, by assessing proportions, within the extracted gas, of the various gases resulting from oil and kerogen.

3. Method according to claim 1, wherein the model compounds are $^{13}C$ labeled by implantation of carbon isotope 13 in precise locations on the model compounds.

4. Method for determining the compositional origin of a gas G from thermal degradation of carbon materials, wherein at least one carbon material type susceptible to generate the gas G is selected, and a model of carbon isotopic composition is built for a gas P generated by thermal degradation of the selected carbon material type, characterized in that the following steps are performed:
   the model of carbon isotopic composition is established by realizing the following steps:
      choosing model compounds of the selected carbon material type;
      calibrating the kinetic effect by pyrolyzing synthesized and $^{13}C$ labeled model compounds in order to determine the precursor effect;
      calibrating the precursor effect by pyrolyzing a mixture of natural model compounds once the kinetic effect is calibrated;
      extending the model of carbon isotopic composition to a complete composition of the selected carbon material type, assuming that either effects, kinetic or precursor, is the same for any other compound of the mixture; and
      extrapolating the model of carbon isotopic compostion to geological conditions
   the model of carbon isotopic composition is calibrated by calibrating a kinetic effect of reaction independently of a precursor effect, defined as a carbon isotopic composition effect of the carbon material type on a carbon isotopic composition of the gas P generated, by pyrolyzinq model compounds of the carbon material type, the model compounds being synthesized and $^{13}C$ labeled;
   a carbon isotopic composition of gas P generated is estimated, using the model of carbon isotopic composition;
   a carbon isotopic composition of the gas G is measured; and
   it is determined whether gas G has been generated from the selected carbon material type, by comparing the measured isotopic composition to the estimated isotopic composition.

* * * * *